United States Patent [19]
Berg et al.

[11] Patent Number: 5,019,217
[45] Date of Patent: * May 28, 1991

[54] SEPARATION OF M-XYLENE FROM O-XYLENE BY EXTRACTIVE DISTILLATION USING ESTERS

[75] Inventors: Lloyd Berg, 1314 S. Third Ave., Bozeman, Mont. 59715; George Bentu, Bozeman, Mont.

[73] Assignee: Lloyd Berg, Bozeman, Mont.

[*] Notice: The portion of the term of this patent subsequent to Dec. 18, 2001 has been disclaimed.

[21] Appl. No.: 476,583

[22] Filed: Feb. 7, 1990

[51] Int. Cl.$^5$ ............................ B01D 3/40; C07C 7/08
[52] U.S. Cl. ........................................ 203/51; 203/56; 203/60; 203/64; 585/866
[58] Field of Search ...................... 203/60, 64, 51, 56; 585/805, 807, 866; 208/313

[56] References Cited

U.S. PATENT DOCUMENTS

| 4,488,937 | 12/1984 | Berg et al. | 203/57 |
| 4,585,526 | 4/1986 | Berg et al. | 585/805 |
| 4,673,465 | 6/1987 | Berg et al. | 203/67 |
| 4,676,872 | 6/1987 | Berg et al. | 203/60 |
| 4,676,875 | 6/1987 | Berg et al. | 203/60 |
| 4,738,755 | 4/1988 | Berg et al. | 585/805 |

Primary Examiner—Wilbur Bascomb, Jr.

[57] ABSTRACT m-Xylene is difficult to separate from o-xylene by conventional distillation or rectification because of the close proximity of their boiling points. m-Xylene can be readily separated from o-xylene by using extractive distillation in which the extractive agent is a higher boiling ester. Typical examples of effective agents are diisononyl adipate, glycerol triacetate and dimethyl phthalate.

1 Claim, No Drawings

[5,019,217]

SEPARATION OF M-XYLENE FROM O-XYLENE BY EXTRACTIVE DISTILLATION USING ESTERS

FIELD OF THE INVENTION

This invention relates to a method for separating m-xylene from o-xylene using certain esters as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

m-Xylene, B.P.=139.1° C. and o-xylene, B.P.=144.4° C. have a relative volatility of 1.12 and are thus difficult to separate by rectification. Extractive distillation would be an attractive method of effecting the separation of m-xylene from o-xylene if agents can be found that (1) will enhance the relative volatility of m-xylene from o-xylene and (2) are easy to recover from the o-xylene, that is, form no azeotrope with o-xylene and boil sufficiently above o-xylene to make the separation by rectification possible with only a few theoretical plates The advantage of using extractive distillation in this separation can be seen from the data shown in Table 1 below.

TABLE 1

Theoretical and Actual Plates Required vs. Relative Volatility for m-Xylene–o-Xylene Separation

| Relative Volatility | Theoretical Plates Required At Total Reflux, 95% Purity | Actual Plates Required, 75% Eff. |
|---|---|---|
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |

The relative volatility of m-xylene to o-xylene is 1.12 and thus require 52 theoretical plates for separation by conventional rectification at total reflux. Plates possessing an efficiency of 75% are commonly employed and thus about 70 actual plates are required, clearly a difficult separation. Several of the agents that we have discovered yield a relative volatility of 1.25 which would reduce the plate requirement to only 36.

Extractive distillation typically requires the addition of an equal amount to twice as much extractive agent as the 3-pentanone and formic acid on each plate of the rectification column The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Previous work on the separation of m-xylene from o-xylene by extractive distillation has been reported by Berg et al. U.S. Pat. No. 4,488,937 described the use of sulfolane; U.S. Pat. No. 4,585,526 used ether-alcohols; U.S. Pat. No. 4,673,465 employed polychloro compounds; U.S. Pat. No. 4,676,875 reported dimethylformamide; U.S. Pat. No. 4,738,755 used benzoates and U.S. Pat. No. 4,836,89 described the use of acetophenone.

OBJECTIVE OF THE INVENTION

The objects of the invention are to provide a process or method of extractive distillation that will enhance the relative volatility of m-xylene to o-xylene in their separation in a rectification column. It is a further object of this invention to identify esters that are stable, can be separated from o-xylene by rectification with relatively few plates and can be recycled to the extractive distillation column with little decomposition.

SUMMARY OF THE INVENTION

The objects of the invention are provided by a process for separation m-xylene from o-xylene which entails the use of certain esters as the agent in extractive distillation.

DETAILED DESCRIPTION OF THE INVENTION

We have discovered that certain esters, either alone or admixed with other esters, will effectively increase the relative volatility of m-xylene from o-xylene and permit the separation of m-xylene from o-xylene by rectification when employed as the agent in extractive distillation. Table 2 lists the esters and their mixtures and the approximate proportions that we have found to be effective. The data in Table 2 was obtained in a vapor-liquid equilibrium still. In every case the starting material was a mixture of m-xylene and o-xylene in the ratio of 30%-70%, 50%-50% or 70%-30%. The relative volatilities are listed for all of mixtures investigated. The esters which are effective are diisononyl adipate, benzyl acetate, diethylene glycol ethyl ether acetate, ethylene glycol diacetate, ethylene glycol butyl ether acetate, ethylene glycol ethyl ether acetate, ethyl phenyl acetate, glycerol triacetate, isobornyl acetate, benzyl benzoate, ethyl benzoate, methyl benzoate, dipropylene glycol dibenzoate, dimethyl glutarate, dibutyl phthalate, diethyl phthalate, dihexyl phthalate, diisodecyl phthalate, ditridecyl phthalate, dimethyl phthalate, diisononyl phthalate dioctyl phthalate, diisooctyl phthalate, diundecyl phthalate, triisononyl mellitate, tributyl phosphate, tricresyl phosphate, methyl salicylate, dimethyl sebacate, dimethyl succinate and triisononyl trimellitate. Diethylene glycol dibenzoate, dimethyl adipate and diundecyl phthalate were effective when used in mixtures with another ester.

Several of the esters whose relative volatilities had been determined in the vapor-liquid equilbrium still were then evaluated in a glass perforated plate rectification column possessing 7.3 theoretical plates and the results listed in Table 3. The agents evaluated were 50% dimethyl adiapate—50% dimethyl glutarate, dimethylphthalate, diethyl phthalate, 50% diethyl phthalate—50% dihexyl phthalate, dibutyl phthalate, dihexyl phthalate, diisooctyl phthalate, diisononyl phthalate and diisodecyl phthalate. These compounds gave a relative volatility in the range of 1.221 to 1.277.

THE USEFULNESS OF THE INVENTION

The usefulness or utility of this invention can be demonstrated by referring to the data presented in Tables 2 and 3. All of the successful extractive distillation agents show that m-xylene can be separated from o-xylene by means of distillation in a rectification column and that the ease of separation as measured by relative volatility is considerable.

TABLE 2

Effective Extractive Distillation Agents

| Compounds | m-Xyl: o-Xyl | Relative Volatility |
|---|---|---|
| Diisononyl adipate | 3:7 | 1.30 |
| " | 5:5 | 1.28 |
| " | 7:3 | 1.28 |
| Benzyl acetate | 3:7 | 1.29 |
| " | 5:5 | 1.17 |
| " | 7:3 | 1.12 |
| Diethylene glycol ethyl ether acetate | 3:7 | 1.18 |
| " | 5:5 | 1.23 |
| Ethylene glycol diacetate | 3:7 | 1.23 |
| " | 5:5 | 1.32 |
| " | 7:3 | 1.19 |
| Ethylene glycol butyl ether acetate | 3:7 | 1.29 |
| " | 5:5 | 1.20 |
| " | 7:3 | 1.10 |
| Ethylene glycol ethyl ether acetate | 3:7 | 1.25 |
| " | 5:5 | 1.16 |
| Ethyl phenyl acetate | 3:7 | 1.22 |
| " | 5:5 | 1.24 |
| " | 7:3 | 1.13 |
| Glycerol triacetate | 3:7 | 1.35 |
| " | 5:5 | 1.20 |
| " | 7:3 | 1.21 |
| Isobornyl acetate | 3:7 | 1.21 |

TABLE 2-continued

Effective Extractive Distillation Agents

| Compounds | m-Xyl: o-Xyl | Relative Volatility |
|---|---|---|
| " | 5:5 | 1.15 |
| " | 7:3 | 1.14 |
| Benzyl benzoate | 3:7 | 1.20 |
| " | 5:5 | 1.18 |
| " | 7:3 | 1.08 |
| Ethyl benzoate | 3:7 | 1.20 |
| " | 5:5 | 1.13 |
| " | 7:3 | 1.16 |
| Methyl benzoate | 3:7 | 1.21 |
| " | 5:5 | 1.26 |
| " | 7:3 | 1.25 |
| Dipropylene glycol dibenzoate | 3:7 | 1.15 |
| " | 5:5 | 1.17 |
| Dimethyl glutarate | 3:7 | 1.24 |
| " | 5:5 | 1.18 |
| " | 7:3 | 1.15 |
| Dibutyl phthalate | 3:7 | 1.36 |
| " | 5:5 | 1.30 |
| " | 7:3 | 1.24 |
| Diethyl phthalate | 3:7 | 1.34 |
| " | 5:5 | 1.33 |
| " | 6:4 | 1.32 |
| Dihexyl phthalate | 3:7 | 1.25 |
| " | 5:5 | 1.25 |
| Diisodecyl phthalate | 3:7 | 1.36 |
| " | 5:5 | 1.23 |
| " | 7:3 | 1.23 |
| Ditridecyl phthalate | 5:5 | 1.20 |
| Dimethyl phthalate | 5:5 | 1.34 |
| Diisononyl phthalate | 5:5 | 1.24 |
| Dioctyl phthalate | 5:5 | 1.26 |
| " | 3:7 | 1.26 |
| " | 5:5 | 1.24 |
| " | 7:3 | 1.21 |
| Diisooctyl phthalate | 3:7 | 1.24 |
| " | 5:5 | 1.26 |
| Diundecyl phthalate | 5:5 | 1.33 |
| Triisononyl mellitate | 3:7 | 1.23 |
| " | 5:5 | 1.26 |
| " | 7:3 | 1.20 |
| Tributyl phosphate | 5:5 | 1.17 |
| " | 7:3 | 1.22 |
| Tricresyl phosphate | 3:7 | 1.25 |
| " | 5:5 | 1.18 |
| " | 7:3 | 1.17 |
| Methyl salicylate | 3:7 | 1.22 |
| " | 5:5 | 1.19 |
| " | 7:3 | 1.35 |
| Dimethyl sebacate | 3:7 | 1.36 |
| " | 5:5 | 1.21 |
| " | 7:3 | 1.23 |
| Dimethyl succinate | 3:7 | 1.16 |
| " | 5:5 | 1.16 |
| Triisononyl trimellitate | 3:7 | 1.16 |
| " | 5:5 | 1.27 |
| Diisononyl adipate - Dihexyl phthalate | 3:7 | 1.15 |
| " | 5:5 | 1.19 |
| Diethylene glycol dibenzoate - dipropylene glycol dibenzoate mixture | 3:7 | 1.23 |
| Diethylene glycol dibenzoate - dipropylene glycol dibenzoate mixture | 5:5 | 1.16 |
| Diethylene glycol dibenzoate - dipropylene glycol dibenzoate mixture | 7:3 | 1.14 |
| Dimethyl glutarate - Dimethyl adipate | 3:7 | 1.28 |
| " " | 5:5 | 1.32 |
| " " | 7:3 | 1.28 |
| Dibutyl phthalate - Diisodecyl phthalate | 3:7 | 1.21 |
| " " | 5:5 | 1.25 |
| " " | 7:3 | 1.13 |
| Diethyl phthalate - Dihexyl phthalate | 3:7 | 1.34 |
| " " | 5:5 | 1.34 |
| " " | 7:3 | 1.33 |
| Diethyl phthalate - Diisodecyl phthalate | 5:5 | 1.42 |
| " " | 3:7 | 1.26 |
| Dihexyl phthalate - dibutyl phthalate | 5:5 | 1.22 |
| Dihexyl phthalate - Diisodecyl phthalate | 3:7 | 1.33 |
| " " | 5:5 | 1.23 |
| " " | 7:3 | 1.23 |
| Dihexyl phthalate - Diisononyl phthalate | 3:7 | 1.26 |

TABLE 2-continued

Effective Extractive Distillation Agents

| Compounds | m-Xyl: o-Xyl | Relative Volatility |
|---|---|---|
| " " | 5:5 | 1.35 |
| " " | 7:3 | 1.21 |
| Dihexyl phthalate - Diisooctyl phthalate | 3:7 | 1.21 |
| " " | 5:5 | 1.28 |
| " " | 7:3 | 1.24 |
| Dihexyl phthalate - Glycerol triacetate | 3:7 | 1.18 |
| " " | 5:5 | 1.11 |
| Diisodecyl phthalate - Diethyl phthalate | 5:5 | 1.26 |
| Ditridecyl phthalate - Diethyl phthalate | 5:5 | 1.32 |
| Diundecyl phthalate - Diethyl phthalate | 5:5 | 1.26 |
| Diundecyl phthalate - Dihexyl phthalate | 5:5 | 1.34 |

TABLE 3

Data From Runs Made In Rectification Column

| Agent | Column | Time, hrs. | Weight % m-Xylene | Weight % o-Xylene | Relative Volatility |
|---|---|---|---|---|---|
| 50% Dimethyl adipate, | Overhead | 2 | 96.7 | 3.3 | 1.221 |
| 50% Dimethyl glutarate | Bottoms | | 87.2 | 12.8 | |
| Dimethyl phthalate | Overhead | 2.3 | 96.5 | 3.5 | 1.277 |
| | Bottoms | | 82.2 | 17.8 | |
| Diethyl phthalate | Overhead | 1.5 | 96.9 | 3.1 | 1.231 |
| | Bottoms | | 90.1 | 9.9 | |
| 50% Diethyl phthalate, | Overhead | 1.5 | 88.1 | 11.9 | 1.235 |
| 50% Dihexyl phthalate | Bottoms | | 79.2 | 20.8 | |
| Dibutyl phthalate | Overhead | 1 | 93.7 | 6.3 | 1.236 |
| | Bottoms | | 75.7 | 24.3 | |
| Dihexyl phthalate | Overhead | 2 | 95.4 | 4.6 | 1.239 |
| | Bottoms | | 81.3 | 18.7 | |
| Diisooctyl phthalate | Overhead | 1 | 92.2 | 7.8 | 1.215 |
| | Bottoms | | 73.3 | 26.8 | |
| Diisononyl phthalate | Overhead | 1 | 93.9 | 6.1 | 1.240 |
| | Bottoms | | 76.1 | 23.8 | |
| Diisodecyl phthalate | Overhead | 1.5 | 63.1 | 36.9 | 1.253 |
| | Bottoms | | 23.7 | 76.3 | |

WORKING EXAMPLES

Example 1

Fifteen grams of m-xylene, 35 grams of o-xylene and 50 grams of diethyl phthalate were charged to a vapor-liquid equilibrium still and refluxed for three hours. Analysis indicated a vapor composition of 32.3% m-xylene, 67.7% o-xylene; a liquid composition of 26.2% m-xylene, 73.8% o-xylene which is a relative volatility of 1.34. Ten grams of m-xylene were added and refluxing continued for another five hours. Analysis indicated a vapor composition of 45.4% m-xylene, 54.6% o-xylene; a liquid composition of 38.5% m-xylene, 61.5% o-xylene which is a relative volatility of 1.33. Ten grams of m-xylene were added and refluxing continued for another thirteen hours. Analysis indicated a vapor composition of 56.3% m-xylene, 43.7% o-xylene; a liquid composition of 49.3% m-xylene, 50.7% o-xylene which is a relative volatility of 1.32.

Example 2

Fifteen grams of m-xylene, 35 g-ams of o-xylene, 25 grams of diethyl phthalate and 25 grams of dihexyl phthalate were charged to the vapor-liquid equilibrium still and refluxed for five hours. Analysis indicated a vapor composition of 21% m-xylene, 79% o-xylene, a liquid composition of 16.5% m-xylene, 83.5% o-xylene which is a relative volatility of 1.34. Ten grams of m-xylene were added and refluxing continued for another twelve hours. Analysis indicated a vapor composition of 49.5% m-xylene, 50.5% o-xylene, a liquid composition of 42.2% m-xylene, 57.8% o-xylene which is a relative volatility of 1.34. Ten grams of m-xylene were added and refluxing continued for another eight hours. Analysis indicated a vapor composition of 71.5% m-xylene, 28.5% o-xylene; a liquid composition of 58.8% m-xylene, 41.2% o-xylene which is a relative volatility of 1.33.

Example 3

A glass perforated plate rectification column was calibrated with m-xylene and o-xylene which possesses a relative volatility of 1.11 and found to have 7.3 theoretical plates. A solution comprising 275 ml. of m-xylene and 50 ml. of o-xylene was placed in the stillpot and heated. When refluxing began, an extractive agent comprising dimethyl phthalate was pumped into the column at a rate of 15 ml/min. The temperature of the extractive agent as it entered the column was 95° C. After establishing the feed rate of the extractive agent, the heat input to the m-xylene—o-xylene in the stillpot was adjusted to give a total reflux rate of 40 ml/min. After 2.5 hours of operation, the overhead and bottom samples of approximately two ml. were collected and analysed by gas chromatography. The overhead analysis was 96.5% m-xylene, 3.5% o-xylene. The bottoms analysis was 82.2% m-xylene, 17.8% o-xylene. Using these compositions in the Fenske equation, with the number of theoretical plates in the column being 7.3, gave an average relative volatility of 1.277 for each theoretical plate.

We claim:

1. A method for recovering m-xylene from mixtures of m-xylene and o-xylene which comprises distilling a mixture of m-xylene and o-xylene in a rectification column in the presence of about one part of an extractive agent per part of m-xylene—o-xylene mixture, recovering m-xylene as overhead product and obtaining the o-xylene and the extractive agent from the stillpot, wherein said extractive agent consists of at least one material selected from the group consisting of diisononyl adipate, benzyl acetate, diethylene glycol ethyl ether acetate, ethylene glycol diacetate, ethylene glycol butyl ether acetate, ethyl phenyl acetate, glycerol triacetate, dimethyl glutarate, tributyl phosphate, tricresyl phosphate, dimethyl sebacate, dimethyl succinate and dimethyl adipate.

* * * * *